(12) United States Patent
Hussain

(10) Patent No.: US 6,423,701 B1
(45) Date of Patent: Jul. 23, 2002

(54) WATER SOLUBLE AMINE ESTERS OF TESTOSTERONE FOR INTRANASAL ADMINISTRATION

(75) Inventor: Anwar A. Hussain, Lexington, KY (US)

(73) Assignee: University of Kentucky, Lexington, KY (US)

(*) Notice: Subject to any disclaimer, the term of this patent is extended or adjusted under 35 U.S.C. 154(b) by 1116 days.

(21) Appl. No.: 08/591,767

(22) Filed: Jan. 25, 1996

(51) Int. Cl.$^7$ .............................. A61K 31/56; C07J 1/00

(52) U.S. Cl. ...................................... 514/178; 552/638

(58) Field of Search .......................... 514/178; 552/641, 552/638

(56) References Cited

U.S. PATENT DOCUMENTS 5,622,944 A * 4/1997 Hale et al. .................. 514/181
5,661,141 A * 8/1997 Petrow ....................... 514/177

* cited by examiner

Primary Examiner—Barbara P. Badio
(74) Attorney, Agent, or Firm—Burns, Doane, Swecker & Mathis, LLP

(57) ABSTRACT

The present invention provides novel water soluble testosterone analogs. These testosterone analogs are suitable for intranasal administration to patients requiring increased plasma testosterone levels. The present invention also provides pharmaceutical compositions containing the testosterone analogs of the present invention. The present invention further provides a method of increasing plasma testosterone levels in patients in need of such treatment comprising the intranasal administration of the water-soluble testosterone analogs and pharmaceutical compositions of the present invention.

15 Claims, 2 Drawing Sheets

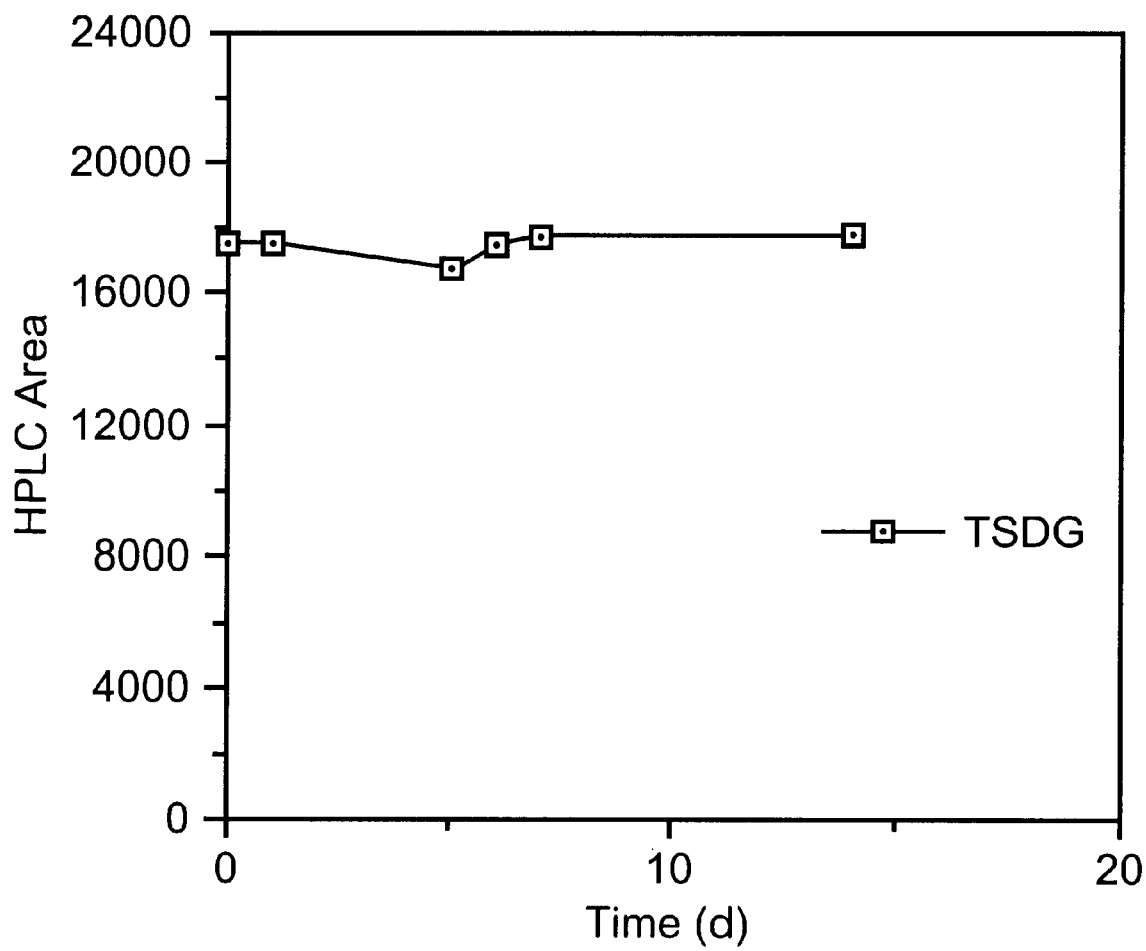

WATER SOLUBLE AMINE ESTERS OF TESTOSTERONE FOR INTRANASAL ADMINISTRATION

FIELD OF THE INVENTION

This invention relates generally to novel water-soluble prodrugs of testosterone suitable for intranasal administration to mammals, including humans, in need of testosterone replacement therapy. More specifically, this invention relates to a water-soluble form of testosterone which is suitable for intranasal administration. This invention also relates to a testosterone replacement therapy which comprises intranasal administration of one or more of the water-soluble forms of testosterone of the present invention.

BACKGROUND

Testosterone (17β-hydroxyandrost-4-en-3-one) and its metabolite, dihydrotestosterone, are the primary endogenous androgenic hormones (androgens). Endogenous androgens are responsible for the normal growth and development of the male sex organs and for development and maintenance of secondary sex characteristics. These effects include the growth and maturation of the prostate, seminal vesicles, penis, and scrotum; the development of male hair distribution, such as facial, pubic, chest, and axillary hair; laryngeal enlargement, vocal cord thickening, alterations in body musculature, and fat distribution.

These compounds also cause retention of nitrogen, sodium, potassium phosphorous, and decreased urinary excretion of calcium. Androgens have also been reported to increase protein anabolism and decrease protein catabolism. Androgens are responsible for the growth spurt of adolescence and for the eventual termination of linear growth brought about by fusion of the epiphyseal growth centers. In children, exogenous androgens accelerate linear growth rate but may cause a disproportionate advancement in bone maturation. Androgens have been reported to stimulate the production of red blood cells by enhancing the production of erythropoietin.

The range of plasma testosterone levels in normal adult men is from 10 to 35 nmol/L (3 to 10 ng/ml). There are clinical conditions in which testosterone levels are decreased from normal levels. Disorders associated with hypotestosteronemia include primary hypogonadism (congenital or acquired), testicular failure due to cryptorchidism, bilateral torsion, Cushing's syndrome, congenital adrenal hyperplasia, hyperprolactinemia, Kinefelter's syndrome, orchitis, sickle cell anemia, Hodgkin's disease, amyloidosis, cirrhosis of the liver, and chronic renal failure. Decreases in plasma testosterone may also accompany surgery, chemotherapy, spinal cord injury, myocardial infarction, severe burns, and toxic damage from exposure to alcohol or heavy metals. In any or all of these conditions it may be desirable for the patient to undergo testosterone replacement therapy.

Testosterone also antagonizes a number of the effects of estrogens, and sometimes is employed clinically for this purpose. This is especially important in the suppression of metastatic carcinoma of the breasts. Testosterone and its esters (e.g., testosterone propionate) and derivatives (e.g., methyltestosterone) also promotes retention of calcium, and may be useful in treatment of osteoporosis.

However, oral administration of testosterone itself is generally ineffective as a means for increasing circulating testosterone levels. When testosterone per se is administered by mouth, it is absorbed into the portal blood and degraded promptly by the liver so that insignificant amounts reach the systemic circulation; when injected parenterally, testosterone is rapidly absorbed from the injection vehicle and rapidly degraded. As a consequence, effective androgen therapy requires either the administration of testosterone in a slowly absorbed dosage form or the administration of modified analogs of testosterone dissolved in oil vehicle. Such chemical modifications represent attempts to retard the rate of metabolism of testosterone, so as to sustain effective blood levels, due to slow conversion of the ester. Three types of modification of the molecule have received widespread clinical application, namely, esterification of the 17β-hydroxyl group, alkylation at the 17α position, and modification of the ring structure, particularly substitutions at the 2, 9, and 11 positions. Most agents actually contain combinations of ring structure alterations and either 17α-alkylation or esterification of the 17β-hydroxyl moiety. Esterification serves to decrease the polarity of the molecule. Consequently, the steroid is more soluble in the fat vehicles used for injection, and release of the steroid into the circulation is slowed. Most esters must be injected parenterally, a route of administration which, because it is painful and inconvenient, is difficult for patients to self-administer in a chronic therapeutic regimen. Furthermore, the more carbon molecules in the acid esterified, the more prolonged is the action of the modified compound. Esters such as testosterone cypionate (testosterone cyclopentanepropionate) and testosterone enanthate (testosterone heptanoate) are typically injected every 1 to 3 weeks. These esters are hydrolyzed before the hormones act; thus the effectiveness of therapy must be monitored by assaying plasma testosterone level with time following administration.

The oral effectiveness of 17α-alkylated androgens (such as methyl-testosterone and methandrostenolone) is due to slower hepatic catabolism than occurs with testosterone itself, so that the alkylated derivatives escape degradation by the liver and reach the systemic circulation. For this reason, 17α-methyl or -ethyl substitution is a common feature of most orally active androgens. Unfortunately, all 17α-alkylated steroids can produce cholestatic hepatitis and jaundice, and other liver function abnormalities such as elevation of plasma alkaline phosphatase and conjugated bilirubin, even at low doses. The most serious complications of 17α-alkylated androgen therapy are the development of peliosis hepatitis (blood-filled cysts in the liver) and hepatoma. While patients with preexisting liver disease are particularly susceptible to these serious side effects, they are frequently seen even in patients without a history of clinical liver disease. 17α-Alkylated drugs also cause an increase in a variety of plasma proteins that are synthesized in the liver. Finally, the relatively infrequent administration of these drugs results in a wide range in postadministration plasma testosterone values.

Although testosterone is known to be absorbed from the nasal cavity, its insolubility in water makes its intranasal administration impractical (see, e.g., Hussain et al., *J. Pharm. Sci.* 73: 1300–1301, 1984). Transdermal preparations of testosterone in which a testosterone-loaded patch is applied each day have recently become available (Testoderm®, Alza Corporation, Palo Alto, Calif.). This therapy avoids the wide swings in serum testosterone values that occur between injections of testosterone esters, and allows for self-administration by the patient. However, the transdermal patch will not produce adequate serum testosterone concentration if applied to nongenital skin. In order to deliver an effective amount of testosterone into the bloodstream, the transdermal patch must be applied directly to a shaved area of the scrotum, where it must be worn for 22–24 hours per day. Furthermore, any testosterone remaining on the skin following removal of the patch may be transferred to the patient's sexual partner. Finally, the transdermal patch suffers from the disadvantage of being extremely expensive.

In view of the foregoing, it is apparent that there exists a need in the art for an improved method of delivery of testosterone for use in testosterone replacement therapy.

Surprisingly, the present inventor has found that intranasal administration of a novel form of testosterone offers significant advantages over the prior art. Those advantages include rapid absorption, and easy and reliable self-administration.

SUMMARY OF THE INVENTION

Accordingly, since parenteral administration of testosterone analogs results in wide swings in plasma testosterone levels, and since chronic self-administration of injectable dosage forms is impractical, and since transdermal dosage forms are expensive and inconvenient, it is an object of the present invention to provide a water-soluble form of testosterone suitable for intranasal administration for use in testosterone replacement therapy.

It is a further aspect of this invention to provide a water-soluble form of testosterone suitable for intranasal administration which is equal to or superior to prior art injectable and transdermal dosage forms in many respects, including effectiveness, but which avoids many of the problems associated with injectable and transdermal dosage forms, while offering superior ease of administration.

It is yet a further aspect of this invention to provide a method of testosterone replacement therapy by intranasally administering the water-soluble form of testosterone of the present invention to a mammalian organism, especially a human, in need of testosterone replacement therapy.

It is a still further aspect of this invention to provide a method for administering testosterone which is equal to or superior to administration of injectable dosage forms in many respects, including effectiveness, but which avoids many of the problems associated with injectable dosage forms, while offering superior ease of administration.

A further aspect of this invention is to provide a pharmaceutical composition suitable for intranasal administration, for use in testosterone replacement therapy. Accordingly, the composition of the present invention comprises an effective amount of the water-soluble form of testosterone of the present invention achieve a desired testosterone level, and a pharmaceutically acceptable carrier therefor.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 3: Time course plot illustrating stability of TSDG in $H_2O$.

DETAILED DESCRIPTION OF THE PREFERRED EMBODIMENTS OF THE INVENTION

Figure 1:
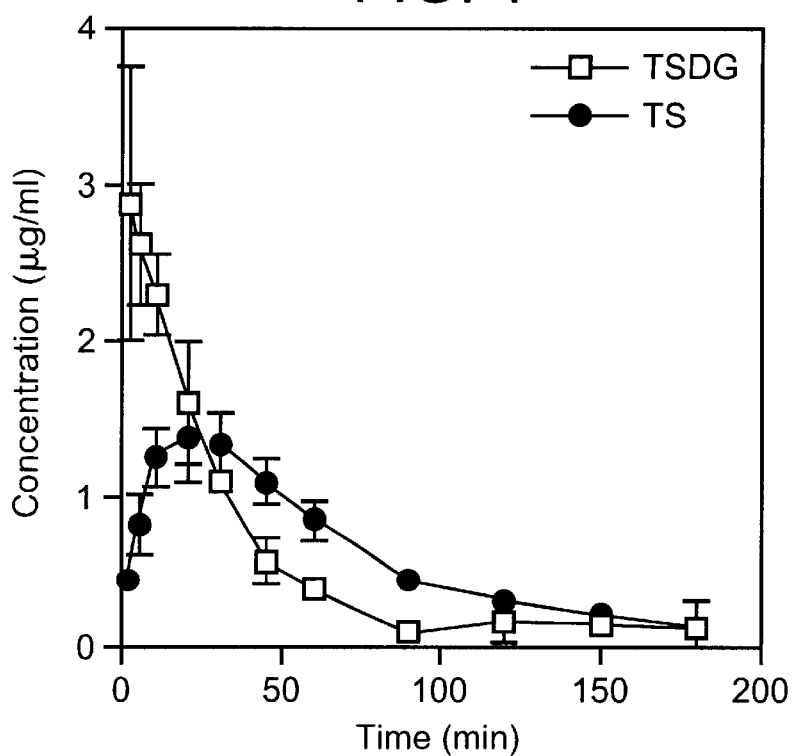
FIG. 1: Time course of plasma levels of testosteronyl, N,N-dimethyl amine glyconate (TSDG) and testosterone (TS) following intranasal administration of TSDG (25.0 mg.kg) in rats.

The present invention is a new water-soluble testosterone prodrug suitable for intranasal administration. The intranasal administration of testosterone prodrugs offers significant clinical advantages over the prior art. Furthermore, the present invention provides a safe, effective and convenient treatment for testosterone deficiency by intranasally administering the water-soluble testosterone prodrugs of the present invention. This avoids the problems associated with the injectable and transdermal dosage forms of testosterone.

The present inventor has found that intranasal administration of the water-soluble testosterone prodrugs of the present invention may be advantageously used in a regimen of testosterone replacement therapy. Intranasal administration of these compounds is as effective as intravenous administration, however, intranasal administration offers the significant advantage that it can be conveniently and painlessly self-administered by the patient.

Preferred testosterone prodrugs will have the following chemical structure:

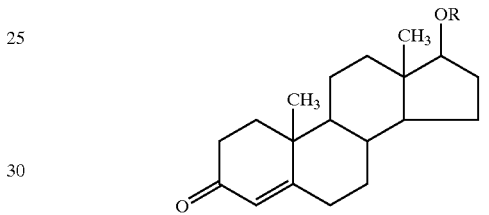

wherein R has the following chemical structure:

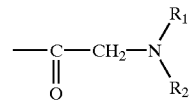

and $R_1$ and $R_2$ are lower alkyl, more preferably straight-chain alkyl, most preferably methyl, ethyl, or propyl. The most preferred water-soluble testosterone prodrug is testosteronyl, N,N-dimethyl amine glyconate (TSDG). Pharmaceutically acceptable salts of the compounds of the present invention are also preferred.

Pharmaceutically acceptable salts include, but are not limited to, salts of organic carboxylic acids, such as acetic, lactic, tartaric, malic, isothionic, lactobionic and succinic acids; organic sulfonic acids, such as methanesulfonic, ethanesulfonic, benzenesulfonic and p-tolylsulfonic acids, and inorganic acids, such as hydrochloric, sulfuric, phosphoric and sulfamic acids.

A further aspect of this invention is a pharmaceutical composition of matter for intranasal testosterone replacement therapy that comprises the water-soluble testosterone prodrugs as described above, mixtures of water-soluble testosterone prodrugs, and/or pharmaceutical salts thereof, and pharmaceutically acceptable carriers therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa., Eighteenth edition (1990).

For therapeutic use in a regimen of testosterone replacement therapy, a water-soluble testosterone prodrug, or its salt, can be conveniently administered in the form of a nasal pharmaceutical composition containing a water-soluble testosterone prodrug, or its salt, and a pharmaceutically acceptable carrier therefor. Suitable carriers for intranasal administration are well known to those skilled in the art and vary with the desired form and mode of administration of the pharmaceutical composition. Typically, the carrier may be a liquid, suspension, semi-solid, gel, or vaporizable carrier, or combinations thereof. In a preferred embodiment, the carrier is a pharmaceutically acceptable aqueous carrier.

The compound of the present invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. To prepare formulations suitable for intranasal administration, solutions and suspensions are sterilized and are preferably isotonic to blood.

The formulations may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided semi-solid carriers or both. Various unit dose and multidose containers, e.g., sealed ampules and vials, may be used, as is well known in the art.

In addition to the ingredients particularly mentioned above, the formulations of this invention may also include other agents conventional in the art for this type of intranasal pharmaceutical formulation.

The present invention is also directed to a method of increasing plasma levels of testosterone in a mammal, e.g., a human, by treating the mammal with an effective amount of a water-soluble testosterone prodrug. For purposes of the present invention, the patient can be any mammal in need of increased plasma levels of testosterone.

The dosage of the water-soluble testosterone prodrug or mixture thereof administered to a patient will vary depending on several factors, including, but not limited to, the age, weight, and species of the patient, the general health of the patient, the severity of the symptoms, the potency of the water-soluble testosterone prodrug, whether the composition is being administered alone or in combination with other agents, the incidence of side effects and the like.

For instance, the desired dose may be administered as 1 to 6 or more subdoses administered at appropriate intervals throughout the day. The compounds may be administered repeatedly over a period of months or years, or it may be slowly and constantly administered to the patient. Higher and lower doses may also be administered.

The daily dose may be adjusted taking into account, for example, the above-identified variety of parameters. Typically, the present compositions may be administered intranasally in an amount of about 0.001 to 100.0 mg/kg body weight/day. However, other amounts may also be administered.

To achieve good plasma concentrations, the active compounds may be administered, for instance, by intranasal administration of an approximate 0.1 to 1M solution of the active ingredient, optionally in saline.

While it is possible for the active ingredient to be administered alone, it is preferably administered in a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the claimed invention.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The method of the present invention may be used in conjunction with other therapies as determined by the practitioner.

The present invention may be used to increase plasma testosterone levels in patients suffering from, for instance, primary hypogonadism (congenital or acquired), testicular failure due to cryptorchidism, bilateral torsion, Cushing's syndrome, congenital adrenal hyperplasia, hyperprolactinemia, Klinefelter's syndrome, orchitis, sickle cell anemia, Hodgkin's disease, amyloidosis, cirrhosis of the liver, and chronic renal failure. Decreases in plasma testosterone may also accompany surgery, chemotherapy, spinal cord injury, myocardial infarction, severe burns, and toxic damage from exposure to alcohol or heavy metals. However, the preceding conditions are not intended to be limiting, and treatment of any condition which requires increased plasma testosterone levels is intended to be encompassed by the present invention.

Having now generally described this invention, the same will be better understood by reference to certain specific examples, which are included herein for purposes of illustration only and are not intended to be limiting of the invention or any embodiment thereof, unless so specified.

EXAMPLE

Intranasal Administration of TSDG

The nasal absorption of the water soluble testosterone prodrug TSDG was studied using an in vivo experimental technique previously described by Huang et al. (*J.Pharmaceut. Sci.,* 74: 608–611, 1985).

Male Sprague-Dawley rats weighing 250–275 gm were used. Animals were fasted overnight before the experiment, but water was given ad libitum. All surgical procedures were performed under sodium pentobarbital anesthesia (40 mg/kg i.p.). An incision was made in the neck, and the trachea was cannulated with a polyethylene tube. A closed tube was inserted through the esophagus to the posterior part of the nasal cavity. The nasopalatine passage was closed with an adhesive agent to prevent drainage of the drug from the nasal cavity to the mouth.

Blood samples were collected from a cannula inserted into the femoral artery. For intravenous administration, the jugular vein was cannulated for administering the dose.

Preparation of the Solutions

Drug solutions at 25 and 50 mg/kg/0.2 ml equimolar doses of TSDG were freshly prepared by using 0.05M phosphate buffer at pH 6.0. For nasal administration, aqueous solutions of TSDG and testosterone were administered through the nostril using a microsyringe. For intravenous administration, the same dose of the drug was injected through the jugular vein.

Sample Collection after Nasal and Intravenous Administrations

Blood samples were collected at 0, 5, 10, 20, 30, 40, 60, 90, 120, 150, and 180 minutes. After immediate centrifugation (3000×g for 3 min), the plasma was separated. The animal was sacrificed after the last sample was obtained, and the samples were then analyzed by HPLC, using the method of Hsyu et al. (*Pharm. Res.* 11:156–159, 1994). Briefly, plasma concentrations of testosterone free base were determined via a HPLC protocol which included solid-phase extraction, separation on a reverse-phase cyano column, and UV detection at 305 nm.

Results

Table 1 shows area under the curve (AUC; μg*hr/ml) after intravenous and intranasal administration of TSDG and testosterone (TS) at doses of 50 mg/kg and 25 mg/kg.

TABLE 1

| DOSE | 50 mg/kg | | 25 mg/kg | |
|---|---|---|---|---|
| ROUTE | Intravenous | Intranasal | Intravenous | Intranasal |
| AUC for TSDG | 2.83 | 2.66 | 1.65 | 1.63 |
| AUC for TS | 3.78 | 3.49 | 1.77 | 1.83 |

The figure shows plasma TSDG and TS levels after intranasal administration at a dose of 25.0 mg/kg. Absorption of TSDG was rapid; plasma levels at all time points were comparable to those following intravenous administration.

Figure 2:
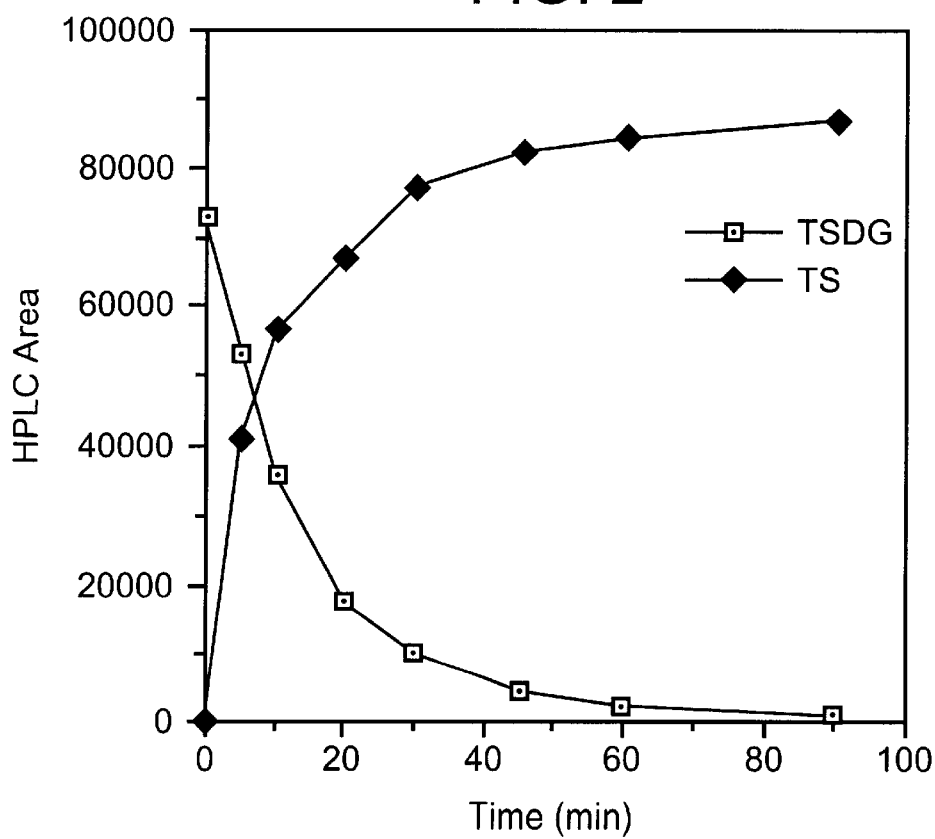
FIG. 2: Time course of conversion of TSDG to TS in liver homogenate.

TSDG was also found to convert rapidly to TS in human liver homogenate as shown in FIG. 2. On the other hand, TSDG was found to be very stable in water, as shown in FIG. 3.

While the invention has been described herein by references to various specific materials, procedures, and examples, it is understood that the invention is not restricted to the particular materials, combinations of materials, and procedures selected for that purpose. Numerous variations of such details can be implied and will be appreciated by those skilled in the art.

What is claimed is:

1. A water-soluble testosterone analog having the following chemical structure:

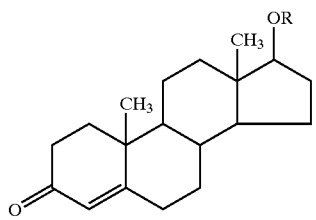

wherein R is:

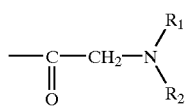

and $R_1$ and $R_2$ are lower alkyl.

2. A testosterone analog according to claim 1, wherein $R_1$ and $R_2$ are straight-chain alkyl.

3. A testosterone analog according to claim 1, wherein $R_1$ and $R_2$ are methyl, ethyl, or propyl.

4. An intranasal pharmaceutical composition comprising a testosterone analog having the following chemical structure:

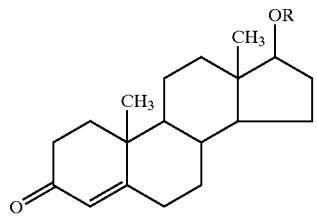

wherein R is:

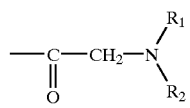

and wherein $R_1$ and $R_2$ are lower alkyl, and a pharmaceutically acceptable carrier therefor.

5. A pharmaceutical composition comprising a testosterone analog according to claim 2 and a pharmaceutically acceptable carrier therefor.

6. A pharmaceutical composition comprising a testosterone analog according to claim 3 and a pharmaceutically acceptable carrier therefor.

7. A method for increasing plasma testosterone levels comprising intranasally administering to a mammal in need of such treatment an effective amount of a testosterone analog having the following structure:

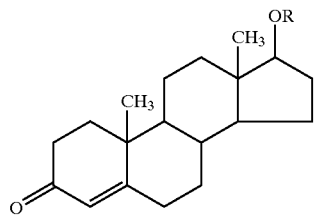

wherein R is:

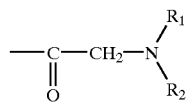

and wherein $R_1$ and $R_2$ are lower alkyl.

8. The method of claim 7, wherein the testosterone analog is administered at a dose of 0.1 to 1.0 mg/kg body weight/day.

9. A method for increasing plasma testosterone levels comprising intranasally administering to a patient in need of such treatment an effective amount of a testosterone analog according to claim 2.

10. The method of claim 9, wherein the testosterone analog is administered at a dose of 0.1 to 1.0 mg/kg body weight/day.

11. A method for increasing plasma testosterone levels comprising intranasally administering to a patient in need of such treatment an effective amount of a testosterone analog according to claim 3.

12. The method of claim 11, wherein the testosterone analog is administered at a dose of 0.1 to 1.0 mg/kg body weight/day.

13. A method for increasing plasma testosterone levels comprising intranasally administering to a patient in need of such treatment an effective amount of the pharmaceutical composition of claim 4.

14. A method for increasing plasma testosterone levels comprising intranasally administering to a patient in need of such treatment an effective amount of the pharmaceutical composition of claim 5.

15. A method for increasing plasma testosterone levels comprising intranasally administering to a patient in need of such treatment an effective amount of the pharmaceutical composition of claim 6.

* * * * *